(12) United States Patent
Smith et al.

(10) Patent No.: US 12,733,920 B2
(45) Date of Patent: Sep. 15, 2026

(54) FIXATION DEVICE, IMPLANT AND IMPLANT ASSEMBLY FOR USE IN TISSUE REPAIR

(71) Applicant: Xiros Limited, Leeds (GB)

(72) Inventors: Liam David Smith, Leeds (GB); Corey James Robinson, Leeds (GB); Martin James Bennett Stanley, Leeds (GB); Bahaa Botros Seedhom, Harrogate (GB)

(73) Assignee: Xiros Limited, Leeds (GB)

( * ) Notice: Subject to any disclaimer, the term of this patent is extended or adjusted under 35 U.S.C. 154(b) by 886 days.

(21) Appl. No.: 17/928,250

(22) PCT Filed: May 28, 2021

(86) PCT No.: PCT/EP2021/064325

§ 371 (c)(1), (2) Date: Nov. 28, 2022

(87) PCT Pub. No.: WO2021/239934

PCT Pub. Date: Dec. 2, 2021

(65) Prior Publication Data

US 2023/0210514 A1 Jul. 6, 2023

(30) Foreign Application Priority Data

May 28, 2020 (GB) ..................................... 2007988

(51) Int. Cl.
*A61B 17/04* (2006.01)
*A61F 2/08* (2006.01)

(52) U.S. Cl.
CPC .. *A61B 17/0401* (2013.01); *A61B 2017/0404* (2013.01); *A61B 2017/0412* (2013.01)

(58) Field of Classification Search
CPC .... A61B 2017/0404; A61B 2017/0412; A61B 2017/0448; A61B 2017/0403;
(Continued)

(56) References Cited

U.S. PATENT DOCUMENTS

2005/0288711 A1* 12/2005 Fallin ................. A61B 17/0401 606/232
2012/0065731 A1 3/2012 Justin et al.
(Continued)

OTHER PUBLICATIONS

International Search Report and Written Opinion of the International Searching Authority, mailed Sep. 16, 2021, for corresponding International Application No. PCT/EP2021/064325, 16 pages.

*Primary Examiner* — Majid Jamialahmadi
(74) *Attorney, Agent, or Firm* — Klarquist Sparkman, LLP

(57) ABSTRACT

An implant assembly for use in tissue repairs includes a fixation device and a flexible elongate implant. The fixation device has a body with a first surface adapted to face towards a bone and a second surface adapted to face away from the bone. Apertures extend through the fixation device body from the first surface to the second surface and serve to attach one end of the flexible elongate implant loop. The flexible elongate implant has a multifilament structure comprising filaments which are of a metallic or non-metallic material. The implant is coupled to the fixation device by passing through the apertures, and has a loop having a first end that is secured to the fixation device and a second end which can be releasably coupled to the fixation device following passage through or around a bone, for securing the implant assembly relative to the bone.

31 Claims, 7 Drawing Sheets

(58) Field of Classification Search
CPC .... A61B 2017/0406; A61B 2017/0408; A61B 17/8061; A61B 17/0401; A61B 17/0487; A61F 2/0811; A61F 2002/0852
See application file for complete search history.

(56) References Cited

U.S. PATENT DOCUMENTS

2012/0089193 A1 4/2012 Stone et al.
2017/0273775 A1 9/2017 Rocco et al.

* cited by examiner

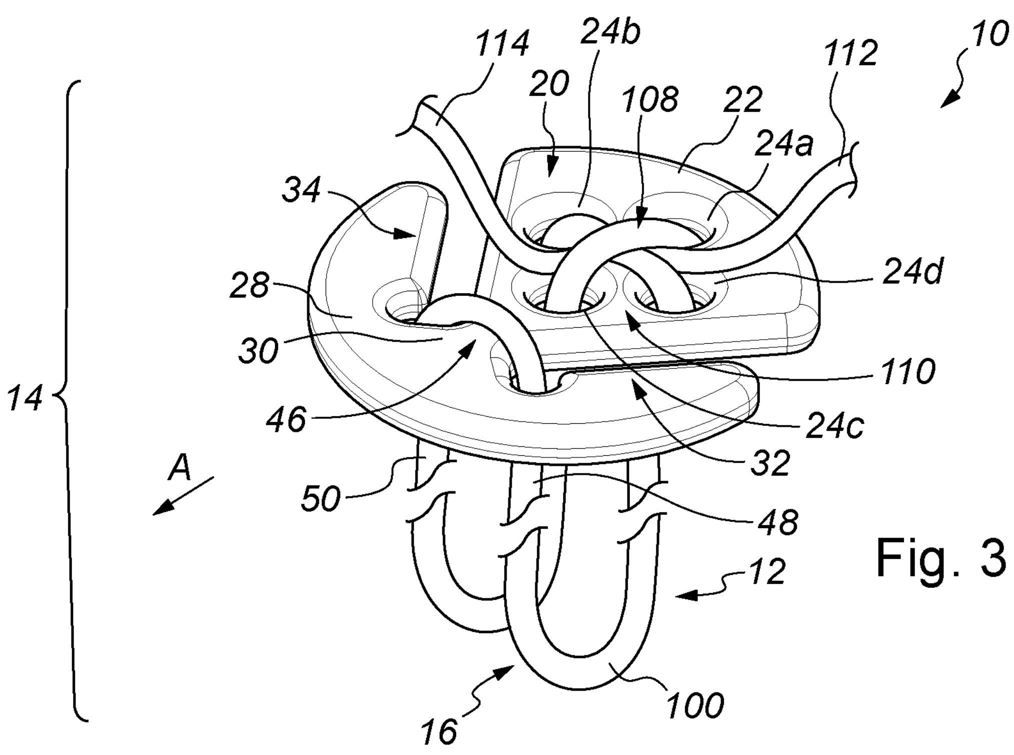
Fig. 3
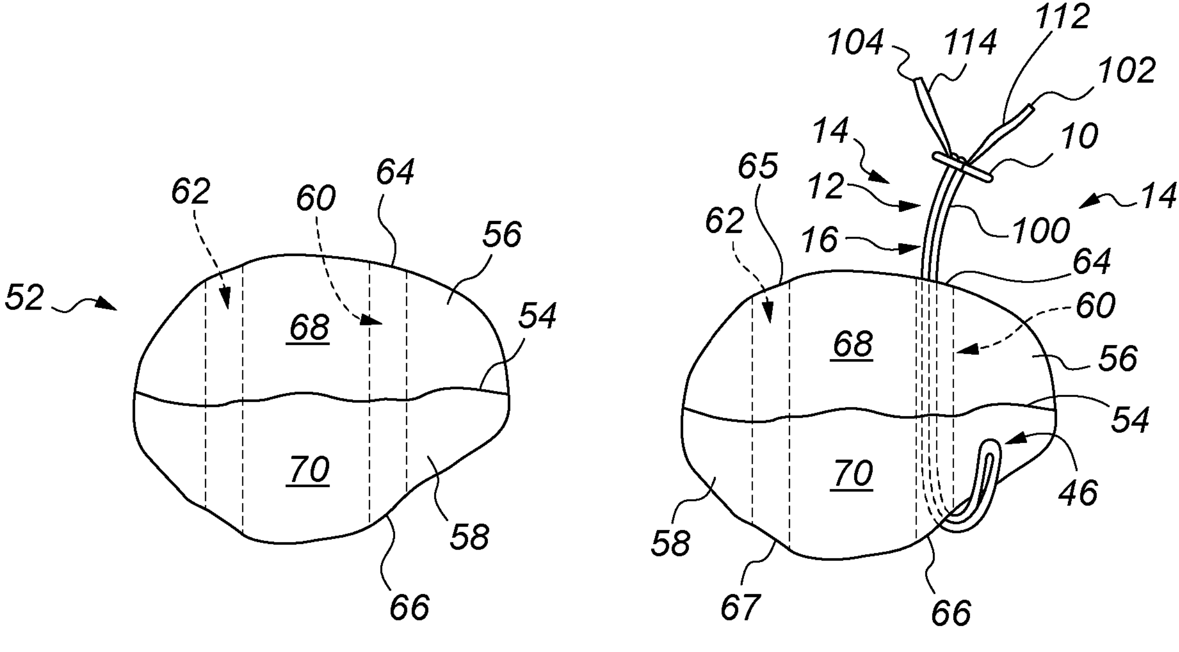
Fig. 4
Fig. 5

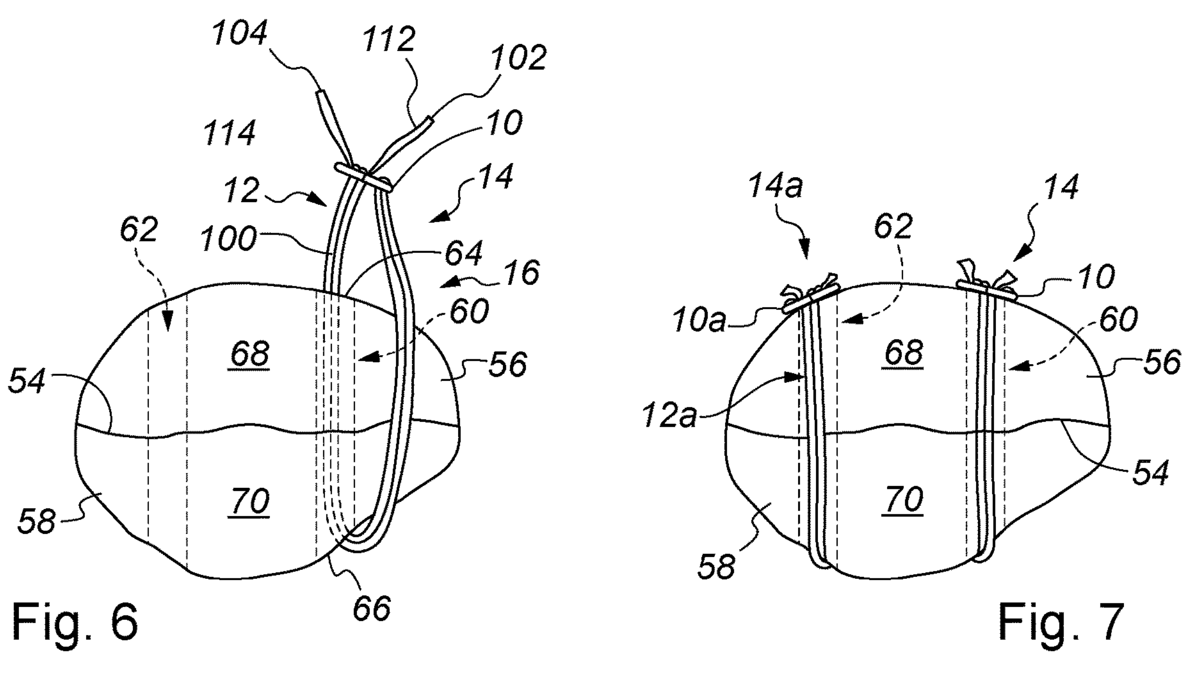
Fig. 6
Fig. 7
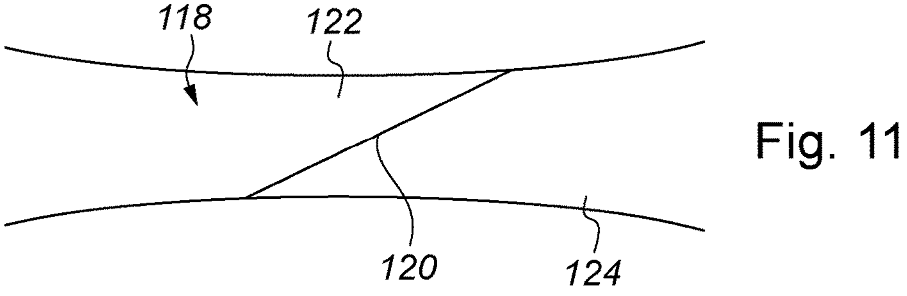
Fig. 11
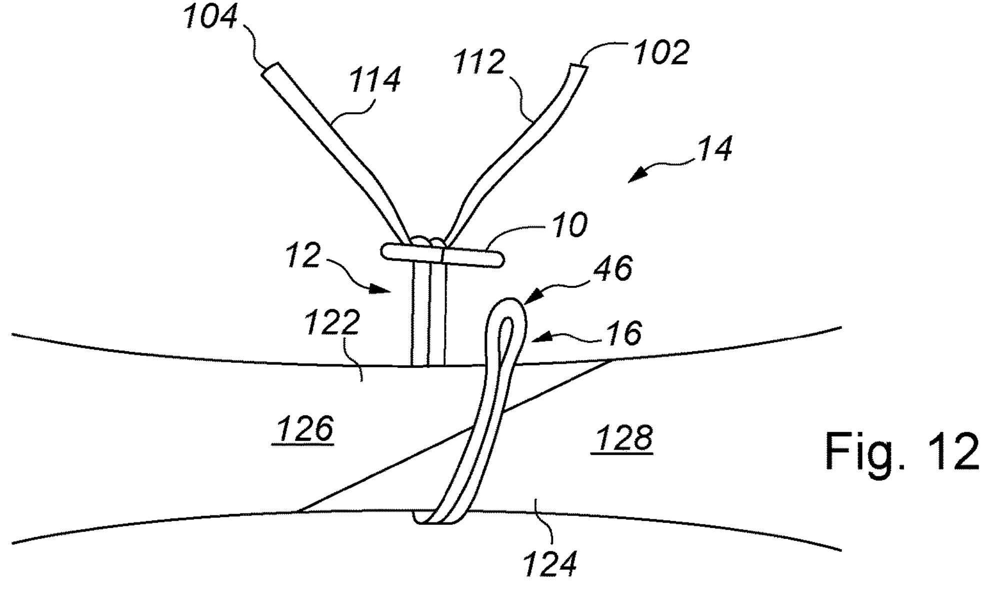
Fig. 12

FIXATION DEVICE, IMPLANT AND IMPLANT ASSEMBLY FOR USE IN TISSUE REPAIR

CROSS REFERENCE TO RELATED APPLICATIONS

This is the U.S. National Stage of International Application No. PCT/EP2021/064325, filed May 28, 2021, which in turn claims priority to Great Britain Patent Application No. GB2007988.5, filed May 28, 2020, which is incorporated herein by reference.

The present disclosure relates to a fixation device for securing an implant relative to a bone. The present disclosure also relates to an implant assembly for use in tissue repair. Methods of tissue repair are also disclosed.

It is well known that complex bone fractures can require a surgical procedure in order to effect a repair. For example, repairing a displaced fracture of the patella (kneecap)—such as a horizontal, vertical or comminuted fracture—can be challenging, typically involving an invasive surgical procedure. The patella fragments must be carefully aligned, and a surgical implant employed to retain the fragments in their proper position during bone healing. There are various procedures for repairing patellar fractures.

One such procedure involves drilling a pair of spaced parallel tunnels though the aligned patella fragments, and then passing one or more malleable metal rod through the tunnels, to secure the fragments together. The rod or rods are often passed into an opening at a first end of one of the tunnels, exiting the tunnel through an opening at a second end before being crossed over and into an opening at a corresponding first end of a second tunnel. The rod is then passed along the second tunnel, exiting through an opening at its second end, before being crossed over to the first end of the first tunnel. The rod is then anchored by twisting end portions of the rod together. This arrangement provides a degree of resistance to torsional loading.

The rods that are used in this procedure typically have a relatively large cross section (around 2 mm in diameter), and are somewhat difficult to manipulate. Maintaining the patella fragments in their proper position during manipulation of the rod or rods can therefore be challenging. Furthermore, portions of the rod are twisted together to secure them, and spare rod material is then cut away. This is difficult to achieve, and tends to leave a large subcutaneous protrusion, which can be uncomfortable for the patient. Finally, in between 30%-40% of the cases a further invasive procedure is required to remove the rods following bone healing.

Alternative techniques have been developed which involve the use of implantable polymeric tapes. The tapes are passed through tunnels in the patella in a similar way to the rods, but are anchored using fixation devices, which may include buttons and interference screws. Whilst this represents an improvement over the use of malleable metal rods, the procedure can still be challenging. In particular, maintaining the patella fragments in their proper position during the procedure can still be difficult.

Other bone fractures can also require a surgical procedure involving the positioning of an implant which serves for securing fragments of the bone together. Oblique fractures of long bones can be particularly challenging, in which a fracture line extends generally transverse to a length of the bone. Malleable metal rods and other relatively invasive devices are often used, with similar challenges to those discussed above.

Bone fracture repair employing metallic cables or ropes has also been known. The cables or ropes comprise twisted filaments of relatively large cross section, and typically have an overall diameter of up to around 2 mm. Consequently the cables are relatively stiff, and so their use in bone fracture repair (e.g. a patella repair, or repair of an oblique fracture of a long bone,) can be challenging, as the cable is difficult to manipulate; in particular where they need to encircle bone. To achieve this an array of cumbersome instruments is required to tension, crimp and cut the cables. In addition, techniques employing such cables require an arrangement of pins/screws in order to secure them to bone and tension the cable, and can require that multiple cables be installed. The pins can be a route for infection to enter the body—where they extend through the skin, bacteria can travel along the pin tract and into the bone. The pins can migrate to an incorrect position in the bone, and are relatively thin and so can be susceptible to facture. Tensioning of the cables can also be challenging, and can have the result that the facture is susceptible to movement.

A need therefore exists to improve upon these known procedures, and on implants and other devices used in the procedures.

According to a first aspect of the present invention, there is provided a fixation device for securing an implant comprising at least one loop relative to a bone, the fixation device comprising:

a first surface adapted to face towards a bone;

a second surface adapted to face away from the bone;

a first portion comprising a plurality of apertures, each aperture extending through the fixation device from the first surface to the second surface, the apertures cooperating to secure a first end of the implant loop;

a second portion coupled to the first portion via a bridge extending between the first and second portions; and first and second channels located between the first and second portions, the channels each extending through the fixation device from the first surface to the second surface and having an open end disposed at a perimeter of the fixation device and a closed end disposed inwardly of the perimeter, the closed end defining a detent for the implant;

in which each channel extends from the perimeter in a direction which is generally towards the other channel, and in which the channels are disposed generally transverse to one another with the bridge located between their closed ends, the channel detents and the bridge cooperating to secure a second end of the implant loop.

The provision of a fixation device comprising such first and second channels may facilitate a surgical procedure involving implantation of the implant in a body of a patient, in particular a surgical procedure to repair a fractured bone, and/or to repair a dislocated joint. The surgical procedure may involve locating the bone-facing first surface of the fixation device adjacent a surface of a bone, securing the first end of the implant loop to the first portion of the fixation device (via the apertures in the first portion), and then passing the loop through and/or around a bone before securing the second end of the loop to the second portion of the fixation device (via the channels and the bridge).

The transverse orientation of the first and second channels may facilitate securing of the second end of the implant loop. The open ends at the perimeter of the fixation device may serve to receive first and second legs of the implant (forming the loop), with an end of the loop located over the bridge. The transverse orientation of the first and second channels may be such that they converge towards an expected direction of loading on the fixation device (by the loop) during use. In this way, engagement of the loop within the first and second channels may be enhanced under applied loading, such loading causing the loop to be urged towards the closed ends of the channels.

The first and second channels may be elongate.

The first and second channels may be substantially straight. The first and second channels may each have a longitudinal axis extending from the open end to the closed end. The first and second channels may be arranged so that the axes are disposed transverse to one another. The axes may intersect, and may intersect at a location which is within the perimeter of the fixation device.

The first and second channels may be disposed in a substantially V-shaped arrangement. The V-shaped arrangement may comprise a root, base, or bottom. The root may be disposed between the closed ends of the channels, and may be defined by the bridge.

The first and second channels may be curved, or at least partly curved. The first and second channels may define or describe an arc. The arcs may intersect at a location which is within the perimeter of the fixation device.

The first and second channels may be disposed in a substantially U-shaped arrangement. The U-shaped arrangement may comprise a root, base, or bottom. The root may be disposed between the closed ends of the channels, and may be defined by the bridge.

The first and second channels may each have a width. The detents of each channel may have a width which is greater than a remainder or main part of the channel. This may serve to resist removal of the implant loop from the channels, by appropriate dimensioning of the main part of the channel and the detent relative to the implant. For example, the width of the main parts of the channels may be such as to provide a close fit with the implant loop, and may be slightly smaller than a cross-sectional width of the implant loop, at least in a relaxed state of the loop. The width of the detents may be approximately the same as, or slightly greater than, the cross-sectional width of the implant loop, at least in a relaxed state. The narrower main parts of the channels may resist transit of the implant loop along the channel from the detents to the open ends. The width or widths may be taken in a plane of the fixation device, such as in a general plane of the first or second surface.

The fixation device may be generally circular in plan view, and may take the general form of a button. The channels may each extend inwardly from a point on the circumference of the fixation device.

The first portion may be generally wedge or pie-shaped. The first portion may comprise an outer surface forming part of the perimeter of the fixation device, and first and second inner surfaces defining parts of the respective first and second channels. The first and second inner surfaces may define side walls of the respective channels. The outer surface may be arcuate. The inner surfaces may be generally straight, but could be arcuate. The outer surface may be a radially outer surface. The inner surfaces may be disposed inwardly of the perimeter.

The second portion may be generally arcuate. The second portion may form a securing portion, which may take the form of a hook/hooking portion, and which can receive the second end of the implant loop to secure the second end. The second portion may comprise an outer surface forming part of the perimeter of the fixation device, and first and second inner surfaces defining parts of the respective first and second channels. The first and second inner surfaces may define side walls of the respective channels. The outer surface may be arcuate. The inner surfaces may each comprise at least a portion which is generally straight, but could be arcuate. The outer surface may be a radially outer surface. The inner surfaces may be disposed inwardly of the perimeter.

The detents may take the general form of an eye or eyelet defined at or by the closed ends of the channels.

The first portion may comprise at least two apertures, and optionally comprises four apertures.

The first surface may be substantially planar. The second surface may be substantially planar. The first portion, second portion and bridge may all be disposed substantially in the same plane.

According to a second aspect of the present disclosure, there is provided an implant assembly comprising the fixation device of the first aspect and an implant comprising at least one loop.

The implant may be adjustable, and may be adjustable in length. The loop may be adjustable, and may be adjustable in length.

The implant may comprise a flexible elongate element which is coupled to the fixation device to form the at least one loop. In use, the flexible elongate element may pass from the second surface side of the fixation device and through one of the apertures to the first surface side, and may then pass from the first surface side through another one of the apertures back to the second surface side, to form the at least one loop. The first end of the implant loop may be formed by a portion of the implant which extends from the second surface side of the fixation device. The second end of the loop may be formed by a portion of the loop which extends from the first surface side of the fixation device.

The flexible elongate element may have a first free end and a second free end, and may pass through apertures of the fixation device so that at least two bone-side loops are formed which each extend from at least one of the apertures at the first surface side of the fixation device. At least one of the bone-side loops may form a support loop, and may comprise the second loop end which is secured by the fixation device. The first loop end may be formed by a further part of the element at the second surface side of the fixation device. At least one fixation loop may be formed which extends from one of the apertures at the second surface of the fixation device to another one of the apertures at the second surface of the fixation device. An adjustable knot arrangement may be formed comprising an adjustable knot which is positionable on the second surface of the fixation device. A first leg may extend from the knot to the first free end of the elongate element and a second leg may extend from the knot to the second free end of the elongate element. The flexible elongate element may be securable to the fixation device by the fixation loop, the fixation loop passing over at least part of the adjustable knot arrangement to clamp the knot arrangement to the fixation device when the bone-side loops are tensioned relative to the fixation device. A length of each of the bone-side loops may be adjustable. An implant of this type is disclosed in International patent application no. PCT/GB2019/053385, filed on 29 Nov. 2019 and entitled “IMPLANT ASSEMBLY AND ASSOCIATED METHODS”, the disclosure of which is incorporated herein by this reference.

The loop (which may be the bone-side loop) may be adapted to be located at least partly within a bone tunnel. The loop (which may be the bone-side loop) may be adapted to be located around an outer surface of a bone, or to pass around part of an outer surface of a bone.

The implant may be of a metallic material, which may be a metal or a metal alloy. Metallic materials may have a yield strength which is significantly greater than polymeric materials typically used in the manufacture of synthetic implants.

Suitable metallic materials may be implantable in the human or animal body. Suitable metallic materials may be selected from the group comprising: steels, including stainless steels; titanium and alloys thereof.

The implant may be a flexible multifilament structure. The implant have a braided or woven structure. Alternatively, the implant may be formed by twisting the filaments together.

The implant may comprise a plurality of yarns or strands, which may be used to form the braided or woven structure. The implant may comprise at least about 10 yarns or strands. The implant may comprise up to about 20 yarns or strands. The implant may comprise between about 10 and about 20 strands, and may comprise between about 12 and about 20 strands. The or each yarn or strand may comprise a plurality of filaments, which may be monofilaments. The filaments may be twisted together to form the yarn or strand. The or each yarn or strand may comprise at least about 10 filaments. The or each yarn or strand may comprise up to about 20 filaments. The or each yarn or strand may comprise between about 10 filaments and about 20 filaments. A suitable number of filaments may be about 19. The or each filament may have a thickness (which may be a diameter) of at least about 20 microns. The or each filament may have a thickness (which may be a diameter) of up to about 30 microns. The or each filament may have a thickness (which may be a diameter) of between about 20 microns and about 30 microns.

An implant, in particular a braided or woven implant, comprising a plurality of yarns or strands which are formed from such filaments, may provide a relatively strong and flexible structure. This may facilitate a procedure to locate the implant in the body, and in particular may facilitate manipulation of the implant, including securing the implant and applying tension. In particular, such an implant may be capable of encircling a bone under light tension. The implant may be of a relatively open structure, which may facilitate an implantation procedure e.g. by providing flexibility, and/or by enabling a part of the implant to be passed back into and along itself, such as to secure an end of the implant or form a loop.

The braided structure may comprise a first set of fibres passing in a first direction around a circumference of the implant, and a second set of fibres passing in a second direction around the circumference of the implant. The first fibres may be disposed transverse to the second fibres, and transverse to a longitudinal axis of the implant. Braid angles may be defined between the fibres and the longitudinal axis. Reference is made to the discussion of a braided structure in PCT/GB2019/053385.

The woven structure may comprise a plurality of longitudinal yarns or strands (warps), and a plurality of transverse yarns or strands (wefts) arranged transverse, suitably perpendicular, to the longitudinal yarns. The longitudinal yarns may extend along/parallel to a main length direction or axis of the implant. The woven structure may be a substantially flat tape. The woven structure may be substantially tubular. The tubular woven structure may comprise one or more side openings. The tubular woven structure may comprise ends which are of reduced width, which may facilitate entry of the ends into a tubular section of the woven structure. Exemplary structures are disclosed in the applicant's prior International Patent Publication nos. WO-2009/109778A2, WO-2013/186525A1 and WO02017/013431A1, the disclosures of which is incorporated herein by this reference.

Further features of the fixation device and implant of the implant assembly may be derived from the text set out elsewhere in this document, in particular in or with reference to the first aspect.

According to a third aspect of the present disclosure, there is provided a method of repairing a fractured bone employing the implant assembly of the second aspect of the present disclosure, the method comprising the steps of:

positioning the implant assembly proximate a fractured bone;

aligning fractured portions of the bone;

directing the loop of the implant away from the first portion of the fixation device and:

A) passing the loop into a first end of a tunnel extending through the aligned fractured portions of the bone and along a length of the tunnel to a second end of the tunnel; or B) passing the loop around at least part of an outer perimeter of the fractured bone;

passing the loop to the second portion of the fixation device, so as to encircle at least part of the bone;

securing the second end of the loop to the fixation device by locating respective first and second legs of the loop in the first and second channels, with the second end of the loop positioned over the bridge; and applying tension to the implant to shorten the loop and thereby clamp the fractured portions of the bone together.

Step A) may further comprise directing the loop into a first end of the tunnel, which may be defined by a first portion of the tunnel in a first bone fragment. The loop may then be directed into a second portion of the tunnel, which may be in a second bone fragment and which may define the second end. It will be understood that further, intermediate parts of the tunnel may be provided in a further bone fragment or fragments, and which may align with the first and second tunnel portions. The loop may then be directed through the second end of the tunnel and passed from the second end to the second portion of the fixation device. The loop may pass from the second end of the tunnel around part of a perimeter of the second bone fragment and part of a perimeter of the first bone fragment to the second portion of the fixation device. This may serve to encircle sections of the first and second fragments of the bone so that they can be clamped together when the implant is tensioned. Where there is a further bone fragment or fragments, such may be clamped between the first and second fragments, and optionally (depending on the nature of the fracture) the loop may pass over part of a perimeter of the further fragment(s).

Step B) may further comprise passing the loop from the fixation device in a first direction around an outer surface of the fractured bone and around the perimeter to the second portion of the fixation device, so that the loop encircles an entire perimeter (or substantially an entire perimeter) of the bone. The method comprising step B) may be a method of bone cerclage.

Further features of the method may be derived from the text set out elsewhere in this document, particularly in or with reference to the first or second aspect of the present disclosure.

According to a fourth aspect of the present disclosure, there is provided an implant assembly for use in tissue repair, the implant assembly comprising:

a fixation device comprising:

a first surface adapted to face towards a bone;

- a second surface adapted to face away from the bone; and
- a plurality of apertures, each aperture extending through the fixation device from the first surface to the second surface; and a flexible elongate implant coupled to the fixation device, the implant having a multifilament structure comprising filaments which are of a metallic material;

in which the implant is coupled to the fixation device by passing through the apertures, and comprises a loop having a first end that is secured to the fixation device and a second end which can be releasably coupled to the fixation device following passage through or around a bone, for securing the implant assembly relative to the bone.

In recent years, synthetic implants have typically been formed from implantable polymeric materials, particularly for relatively flexible implants such as synthetic ligaments and tendons. Relatively rigid (but malleable) metallic implants have been used in other scenarios, including in repairing bone fractures using malleable metallic rods, as discussed above.

The inventors have recognised that there are many scenarios in which relatively flexible implants could be employed, by using an implant which is a multifilament structure comprising filaments of a metallic material. An implant of this type has relatively high yield strength in tension, when compared to prior flexible polymeric implants, whilst being more flexible under transverse loading than prior malleable metallic implants (which tend to maintain a deformed shape in the absence of a relatively significant applied deformation load). The implant of the present disclosure may therefore have a relatively high strength under applied loading (during use), whilst being relatively easy to manipulate in a surgical procedure to implant the assembly in the body of a patient.

The metallic material may be a metal or a metal alloy. Suitable metallic materials may be implantable in the human or animal body. Suitable metallic materials may be selected from the group comprising: steels, including stainless steels; titanium and alloys thereof.

The multifilament structure may be a braided or woven structure. Alternatively the multifilament structure may be formed by twisting the filaments together.

The implant may comprise a plurality of yarns or strands, which may be used to form the braided or woven structure. The implant may comprise at least about 10 yarns or strands.

The implant may comprise up to about 20 yarns or strands. The implant may comprise between about 10 and about 20 strands, and may comprise between about 12 and about 20 strands. The or each yarn or strand may comprise a plurality of filaments, which may be monofilaments. The filaments may be twisted together to form the yarn or strand. The or each yarn or strand may comprise at least about 10 filaments. The or each yarn or strand may comprise up to about 20 filaments. The or each yarn or strand may comprise between about 10 filaments and about 20 filaments. A suitable number of filaments may be about 19. The or each filament may have a thickness (which may be a diameter) of at least about 20 microns. The or each filament may have a thickness (which may be a diameter) of up to about 30 microns. The or each filament may have a thickness (which may be a diameter) of between about 20 microns and about 30 microns.

An implant, in particular a braided or woven implant, comprising a plurality of yarns or strands which are formed from such filaments, may provide a relatively strong and flexible structure. This may facilitate a procedure to locate the implant in the body, and in particular may facilitate manipulation of the implant, including securing the implant and applying tension. In particular, such an implant may be capable of encircling a bone under light tension. The implant may be of a relatively open structure, which may facilitate an implantation procedure e.g. by providing flexibility, and/or by enabling a part of the implant to be passed back into and along itself, such as to secure an end of the implant or form a loop.

The braided structure may comprise a first set of fibres passing in a first direction around a circumference of the implant, and a second set of fibres passing in a second direction around the circumference of the implant. The first fibres may be disposed transverse to the second fibres, and transverse to a longitudinal axis of the implant. Braid angles may be defined between the fibres and the longitudinal axis. Reference is made to the discussion of a braided structure in PCT/GB2019/053385.

The woven structure may comprise a plurality of longitudinal yarns or strands (warps), and a plurality of transverse yarns or strands (wefts) arranged transverse, suitably perpendicular, to the longitudinal yarns. The longitudinal yarns may extend along/parallel to a main length direction or axis of the implant. The woven structure may be a substantially flat tape. The woven structure may be substantially tubular. The tubular woven structure may comprise one or more side openings. The tubular woven structure may comprise ends which are of reduced width, which may facilitate entry of the ends into a tubular section of the woven structure. Exemplary structures are disclosed in the applicant's prior International Patent Publication nos. WO-2009/109778A2, WO-2013/186525A1 and WO02017/013431A1.

The fixation device may comprise a first portion comprising the plurality of apertures. The apertures may cooperate to secure a first end of the implant loop.

The fixation device may comprise a second portion coupled to the first portion via a bridge extending between the first and second portions.

The fixation device may comprise first and second channels located between the first and second portions, the channels each extending through the fixation device from the first surface to the second surface and having an open end disposed at a perimeter of the fixation device and a closed end disposed inwardly of the perimeter, the closed end defining a detent for the implant.

Each channel may extend from the perimeter in a direction which is generally towards the other channel. The channels may be disposed generally transverse to one another with the bridge located between their closed ends, the channel detents and the bridge cooperating to secure the second end of the implant loop.

The implant may be adjustable, and may be adjustable in length. The loop may be adjustable, and may be adjustable in length. A suitable implant is disclosed in International patent application no. PCT/GB2019/053385, filed on 29 Nov. 2019 and entitled "IMPLANT ASSEMBLY AND ASSOCIATED METHODS". Reference is made to the discussion above for optional further features of the implant.

Further features of the fixation device and implant of the implant assembly may be derived from the text set out elsewhere in this document, in particular in or with reference to the first to third aspects. In particular options, the fixation device may be the fixation device of the first or sixth aspect, which may have any of the optional further features described in this document.

According to a fifth aspect of the present disclosure, there is provided a method of repairing a fractured bone employing the implant assembly of the fourth aspect of the present disclosure, the method comprising the steps of:

positioning the implant assembly proximate a fractured bone;

aligning fractured portions of the bone;

directing the loop of the implant away from the first portion of the fixation device and:

A) passing the loop into a first end of a tunnel extending through the aligned fractured portions of the bone and along a length of the tunnel to a second end of the tunnel; or B) passing the loop around at least part of an outer perimeter of the fractured bone;

passing the loop to the second portion of the fixation device, so as to encircle at least part of the bone;

coupling the second end of the loop to the fixation device; and applying tension to the implant to shorten the loop and thereby clamp the fractured portions of the bone together.

Step A) may further comprise directing the loop into a first end of the tunnel, which may be defined by a first portion of the tunnel in a first bone fragment. The loop may then be directed into a second portion of the tunnel, which may be in a second bone fragment and which may define the second end. It will be understood that further, intermediate parts of the tunnel may be provided in a further bone fragment or fragments, and which may align with the first and second tunnel portions. The loop may then be directed through the second end of the tunnel and passed from the second end to the second portion of the fixation device. The loop may pass from the second end of the tunnel around part of a perimeter of the second bone fragment and part of a perimeter of the first bone fragment to the second portion of the fixation device. This may serve to encircle sections of the first and second fragments of the bone so that they can be clamped together when the implant is tensioned. Where there is a further bone fragment or fragments, such may be clamped between the first and second fragments, and optionally (depending on the nature of the fracture) the loop may pass over part of a perimeter of the further fragment(s).

Step B) may further comprise passing the loop from the fixation device in a first direction around an outer surface of the fractured bone and around the perimeter to the second portion of the fixation device, so that the loop encircles an entire perimeter (or substantially an entire perimeter) of the bone. The method comprising step B) may be a method of bone cerclage.

Further features of the method may be derived from the text set out elsewhere in this document, particularly in or with reference to the first to fourth aspects of the present disclosure.

According to a sixth aspect of the present invention, there is provided a fixation device for securing an implant comprising at least one loop relative to a bone, the fixation device comprising:

a first surface adapted to face towards a bone;

a second surface adapted to face away from the bone;

a first portion comprising a plurality of apertures, each aperture extending through the fixation device from the first surface to the second surface, the apertures cooperating to secure a first end of the implant loop;

a second portion coupled to the first portion via a bridge extending between the first and second portions; and a channel located between the first and second portions, the channel having an open end and a closed end defining a detent for the implant;

in which the bridge is located at the closed end of the channel, the channel detent and the bridge cooperating to secure a second end of the implant loop.

The first portion may be disposed generally in a plane, which may be a first plane. The second portion may be disposed generally in a plane, which may be a second plane. The second portion may be disposed in substantially the same plane as the first portion. The first and second planes may be substantially parallel. The second portion may be disposed in a different plane to the first portion, and/or may extend out of a plane containing the first portion. The first and second planes may be disposed transverse to one another, optionally perpendicular.

Further features of the fixation device may be derived from the text set out elsewhere in this document, in particular in or with reference to the first aspect. This may apply particularly to features and/or terms which are common to the fixation devices of the first and sixth aspects.

According to a seventh aspect of the present disclosure, there is provided an implant assembly comprising the fixation device of the sixth aspect and an implant comprising at least one loop.

The implant may be adjustable, and may be adjustable in length. The loop may be adjustable, and may be adjustable in length. The implant may be of a metallic material, which may be a metal or a metal alloy. The implant may be a flexible multifilament structure. The implant have a braided or woven structure, or may be formed by twisting the filaments together.

Further features of the fixation device and implant of the implant assembly may be derived from the text set out elsewhere in this document, in particular in or with reference to one or more of the first to fifth aspects. This may apply particularly to features and/or terms which are common to the fixation devices and/or implant assemblies defined in the first to fifth aspects.

According to an eighth aspect of the present disclosure, there is provided a method of repairing tissue employing the implant assembly of the seventh aspect of the present disclosure.

The method may comprise the steps of:

positioning the implant assembly proximate a bone;

directing the loop of the implant away from the first portion of the fixation device and:

A) passing the loop into a first end of a tunnel extending through a bone and along a length of the tunnel to a second end of the tunnel; or B) passing the loop around at least part of an outer perimeter of the bone;

passing the loop to the second portion of the fixation device; and securing the second end of the loop to the fixation device by locating the loop in the channel with the second end of the loop positioned over the bridge.

The method may be a method of repairing a fractured bone, a joint (e.g. a dislocated joint). The method may comprise steps which correspond to those set out elsewhere in this document, particularly in or with reference to the third and/or fifth aspects.

The methods disclosed in this document may be methods of repairing bone tissue such as a fractured bone, or a joint (e.g. a dislocated joint) comprising bone and soft tissues. It is also conceivable that the methods may be for repairing other tissue including soft tissue (such as a damaged ligament or tendon). The implants, implant assemblies and fixation devices disclosed in this document may have a use in the repair of any such tissue.

Embodiments of the present invention will now be described, by way of example only, with reference to the accompanying drawings, in which:

FIG. 3 is a view of the implant assembly which corresponds to FIG. 2, but showing a loop of the implant secured to the fixation device;

FIG. 4 is a front view of a fractured human patella bone;

FIGS. 5 to 7 are views of the fractured patella bone which correspond to FIG. 4, showing steps in a method of implanting the implant assembly of FIGS. 2 and 3;

Figure 2:
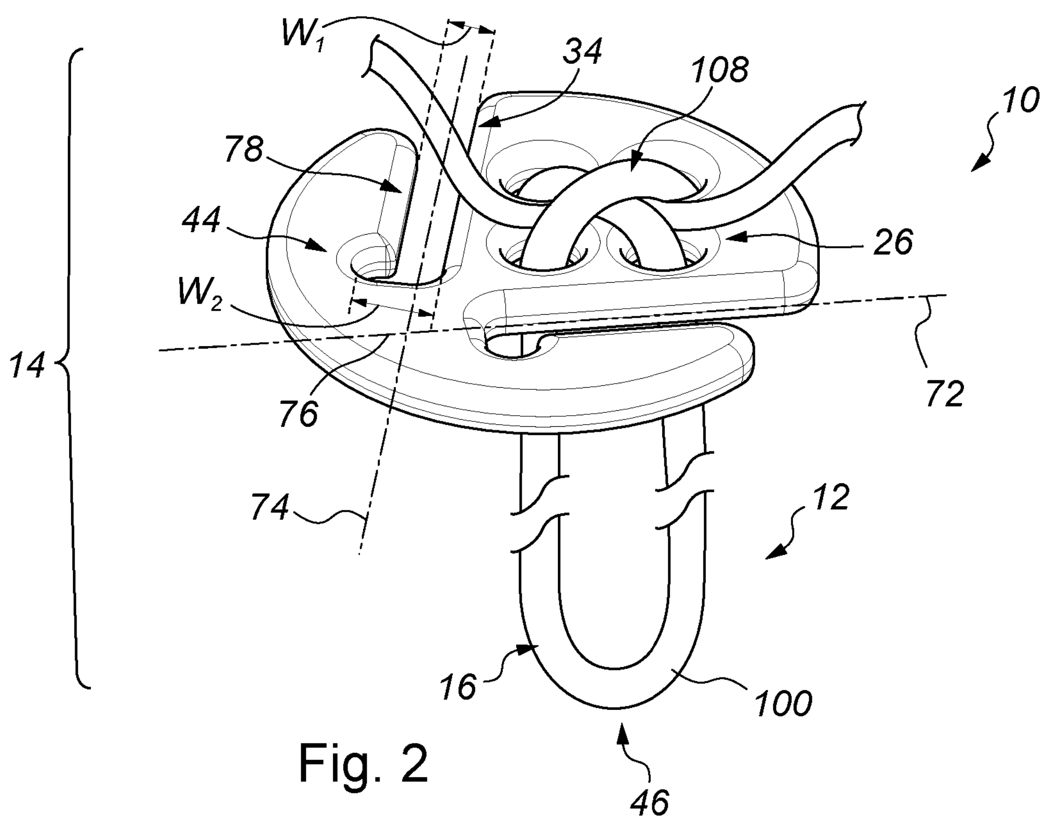
FIG. 2 is a perspective view, taken from above, of an implant assembly in accordance with an embodiment of the present invention, comprising the fixation device of FIG. 1 and an implant.
Figure 13:
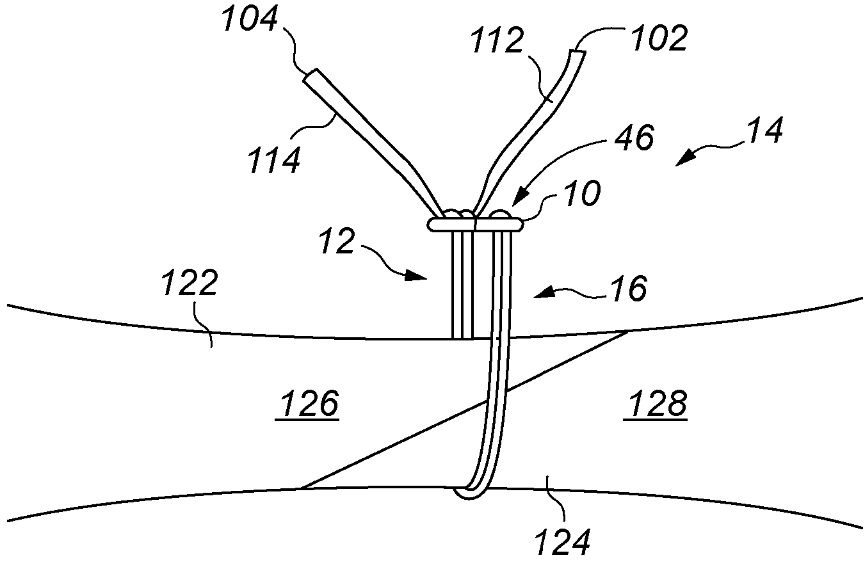
Figure 14:
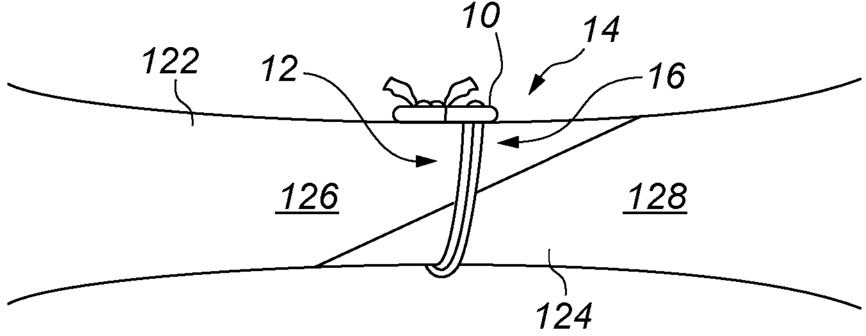
Figure 15:
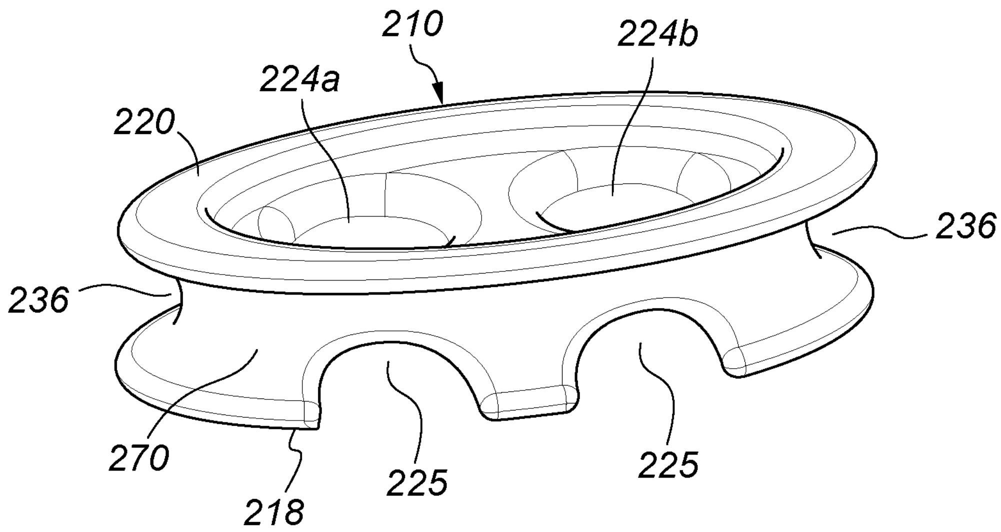
Figure 16:
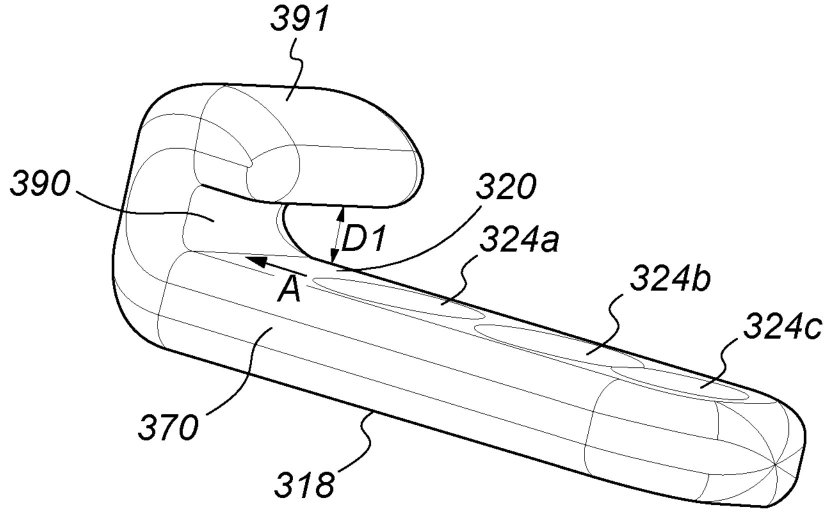
Figure 17:
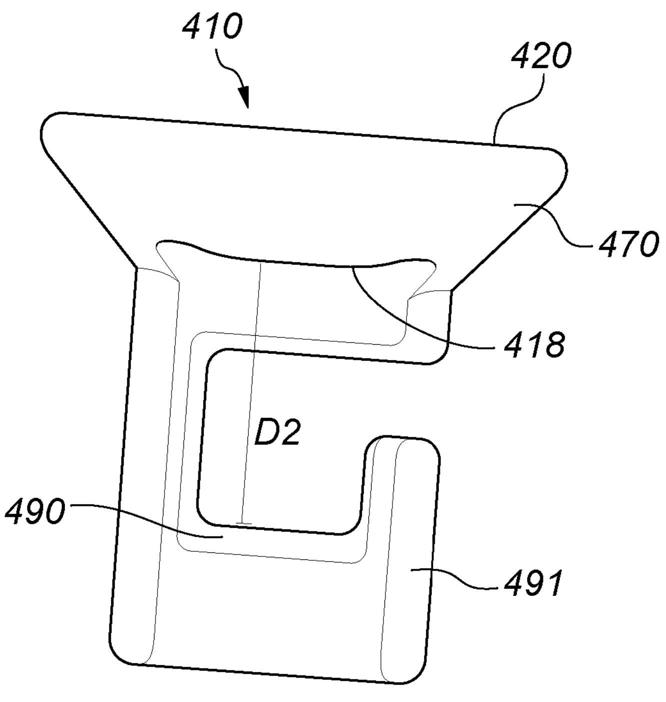
Figure 18:
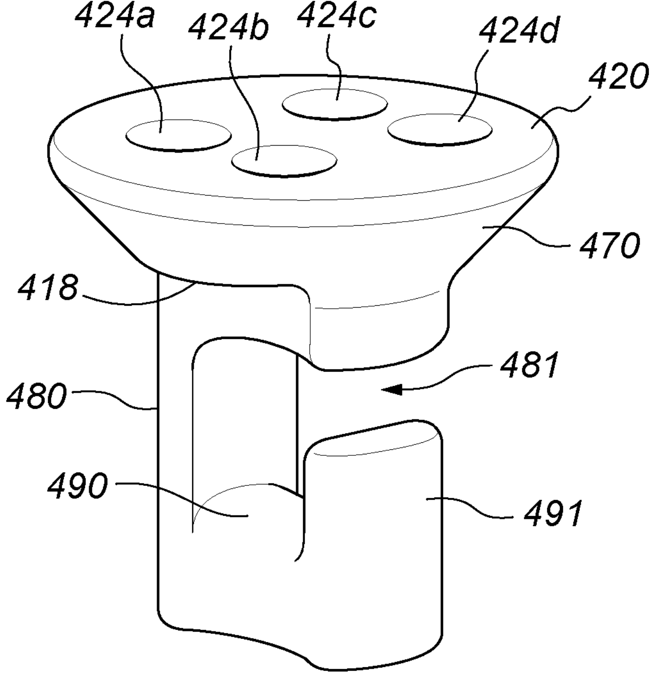

FIG. 11 (presented on the same sheet as FIG. 7) is a front view of a fractured human tibia bone;

FIG. 12 (presented on the same sheet as FIG. 7) is a view of the fractured tibia bone which correspond to FIG. 11, showing steps in a method of implanting the implant assembly of FIGS. 2 and 3; and FIGS. 13 and 14 are views of the fractured tibia bone showing further steps in the method;

FIG. 15 discloses an alternative configuration of a fixation device in accordance with the invention;

FIG. 16 discloses a further alternative configuration of a fixation device in accordance with the invention;

FIGS. 17 and 18 show different views of a still further alternative configuration of a fixation device in accordance with the invention.

Figure 1:
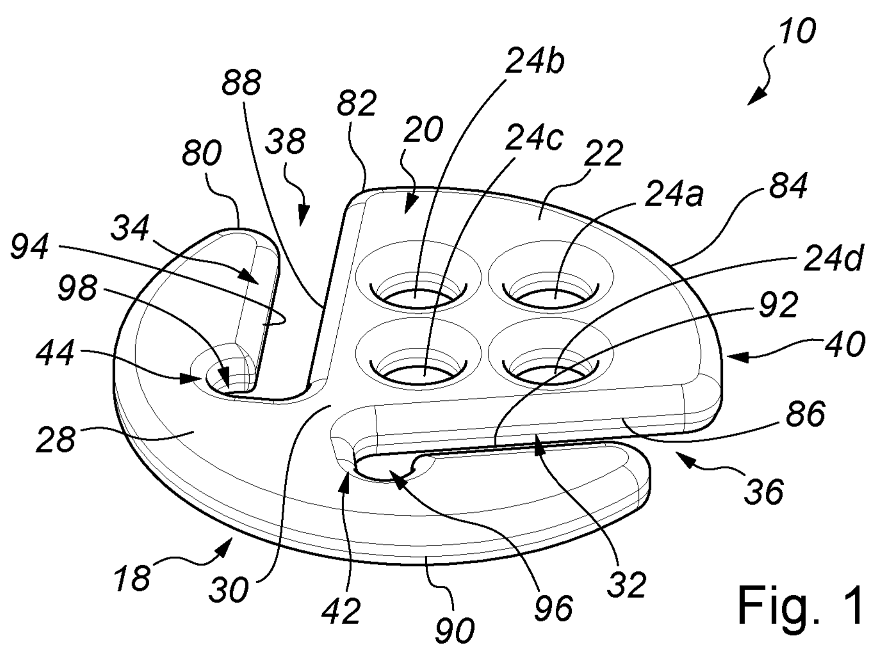
FIG. 1 is a perspective view of a fixation device in accordance with an embodiment of the present invention.

Turning firstly to FIG. 1, there is shown a perspective view of a fixation device in accordance with an embodiment of the present invention, the fixation device indicated generally by reference numeral 10. FIG. 2 is a perspective view of the fixation device which corresponds to FIG. 1, but which shows an implant in accordance with an embodiment of the present invention coupled to the fixation device 10, the implant indicated generally by reference numeral 12. The fixation device 10 and the implant 12 together form an implant assembly 14. The implant assembly 14 has a use in tissue repair, in particular in the repair of bone tissue, such as where a bone has suffered a fracture. However, it is conceivable that the implant assembly 14 could have a use in the repair of other tissue, including soft tissue. The implant assembly 14 may have a use in the repair of a synovial joint comprising two or more bones and associated soft tissue such as one or more ligament and/or tendon, or conceivably in the repair of such soft tissue itself.

In the illustrated example, the fixation device 10 is for securing the implant 12 relative to a bone, the implant comprising at least one loop 16. The fixation device generally comprises a first surface 18 which is adapted to face towards a bone, and a second surface 20 which is adapted to face away from the bone. The fixation device 10 also comprises a first body portion 22 comprising a plurality of apertures, the illustrated device comprising four apertures 24*a* to 24*d*. The apertures 24*a* to 24*d* each extend through the fixation device 10 from the first surface 18 to the second surface 20, and cooperate to secure a first end 26 of the implant loop 16.

The fixation device 10 also comprises a second portion 28 which is coupled to the first body portion 22 via a bridge 30 which extends between the first and second portions. At least one channel is located between the first and second portions 22 and 28. In the illustrated embodiment, first and second channels 32 and 34 are provided which are located between the first and second portions 22 and 28, each channel extending through the fixation device 10 from the first surface 18 to the second surface 20. The channels 32 and 34 each have respective open ends 36, 38 disposed at a perimeter 40 of the fixation device 10, and respective closed ends 42, 44 which are disposed inwardly of the perimeter, the closed ends defining detents for the implant 12.

As can best be seen in FIG. 1, the channels 32 and 34 each extend from the perimeter 40 in a direction which is generally towards the other channel. The channels 32 and 34 are also disposed generally transverse to one another, with the bridge 30 located at, and between, their closed ends 42 and 44. The detents defined by the closed ends 42 and 44 of the channels 32 and 34, together with the bridge 30, cooperate to secure a second end 46 of the implant loop 16, as can be seen in the perspective view of FIG. 3, in which the second end 46 has been located in the channels 32 and 34, passing over the bridge 30.

The provision of a fixation device comprising detents such as channels, arcuate slots, channels or other means of releasable attachment or securing for a closed loop end of a flexible implant facilitates a surgical procedure which involves implantation of the implant 12 in a body of a patient, in particular a surgical procedure to repair a fractured bone and/or to repair a dislocated joint. This will be described in more detail below. However, it is conceivable that the fixation device 10 could have a use in other surgical techniques, including but not limited to repair of soft tissue such as a damaged ligament or tendon, and in particular in an anterior cruciate ligament (ACL) repair technique.

The transverse orientation of the first and second channels 32 and 34 may facilitate securing of the second end 46 of the implant loop 16. In particular, the open ends 36 and 38 of the channels serve to receive first and second legs 48 and 50 of the implant 12 (forming the loop 16), with the end 46 of the loop located over the bridge 30. This transverse orientation is such that the channels 32 and 34 converge towards an expected direction of loading on the fixation device 10 (by the loop 16) during use, as indicated by the arrow A in FIG. 3. In this way, engagement of the loop 16 within the first and second channels 32 and 34 is enhanced under applied loading, such loading causing the loop to be urged towards the closed ends 42 and 44 of the channels.

A surgical procedure employing the implant assembly 14 will now be described, with reference to FIGS. 4 to 7. FIG. 4 shows a human patella bone 52 (or kneecap) which has suffered a transverse displaced fracture, as indicated by the fracture line 54 in the drawings. The patella 52 has fractured into two separate fragments comprising an upper or superior fragment 56 and a lower or inferior fragment 58.

As a preparatory step to implantation of the assembly 14, the upper and lower patella fragments 56 and 58 have been realigned along the fracture line 54, and a pair of laterally spaced bone tunnels 60 and 62 have been formed which extend in a generally superior-inferior direction. FIGS. 5 to 7 are views of the patella 52 which correspond to FIG. 4, and which show steps in the method of implanting the assembly 14.

The method involves positioning the implant assembly 14 proximate the fractured patella 52 with the upper and lower fragments 56 and 58 aligned, as discussed above. It will be understood that the fragments 56 and 58 will typically be held in alignment using suitable surgical equipment, for example a clamping assembly (not shown). The loop 16 of the implant 12 is directed away from the first portion 20 of the fixation device 10, and is passed into a first open end 64 of the bone tunnel 60. This is typically achieved using a suture coupled to the implant loop 16, using a guide such as a blunt needle attached to the suture (not shown).

The needle is directed through the open end 64 and along a length of the tunnel 60 to a second open end 66, trailing the implant loop 16 behind it. The suture is removed from the tunnel 60 so as to expose the second end 46 of the implant loop 16, as shown in FIG. 5. The second end 46 is then passed to the fixation device 10 and is secured to the fixation device by hooking the second end 46 of the loop 16 over the second portion 28 of the fixation device, so that it is positioned as shown in FIG. 3. The implant loop 16 then encircles parts of the upper and lower bone fragments 56 and 58, as shown in FIG. 6, the loop passing over outer surfaces 70 and 68 of the bone fragments 58 and 56, as shown in the drawing.

The implant 12 is initially coupled to the fixation device 10 so as to provide a degree of slack in the loop 16, to facilitate its location in the bone tunnel 60, and coupling of its second end 46 to the fixation device as shown in FIG. 6. The slack in the implant 12 can then be taken-up, effectively reducing a length of the loop 16 so as to reduce the fixation device 10 onto the outer surface 68 of the upper patella fragment 56. This is shown in FIG. 7, and is achieved by pulling on free ends 102 and 104 of the implant 12, as will be described in more detail below. The upper and lower patella fragments 56 and 58 are then drawn together and securely clamped along the fracture line 54. The implant assembly 14 remains in place during bone healing so as to ensure correct alignment of the fragments during the healing process.

A further implant assembly 14*a* is then located in the second bone tunnel 62, as shown in FIG. 7. The structure of the implant assembly 14*a*, and its method of implantation, is the same as that described above in relation to the implant assembly 14. The provision of two such implant assemblies 14 and 14*a* provides for secure coupling of the patella fragments 56 and 58 during the healing process, and resists loading on the patella 52 during use, in particular torsional (twisting) loading, which can otherwise tend to separate the fragments.

The fixation device 10, implant 12 and its method of adjustment will now be described in more detail.

As shown in FIG. 1, the channels 32 and 34 of the fixation device are each elongate, and are substantially straight. The channel 32 has a longitudinal axis 72 (FIG. 2) which extends from its open end 36 to its closed end 42. Similarly, the channel 34 has a longitudinal axis 74 extending from its open end 38 to its closed end 44. The channels 32 and 34 are arranged so that their axes 72 and 74 are disposed transverse to one another, and intersect at a location 76, which is disposed within the perimeter 40 of the fixation device 10. The channels 32 and 36 are effectively disposed in a substantially V-shaped arrangement, comprising a root, base or bottom which is disposed between the closed ends 42 and 44 of the channels, and which is defined by the bridge 30.

The channels 32 and 34 each have a respective width, which is illustrated in FIG. 2 with reference to the second channel 34. The channel width $W_1$ is a width of a main part 78 of the channel, having substantially straight sides. The detent formed by the closed end 44 of the channel 34 also has a width $W_2$ which is greater than the width $W_1$ of the main part 78 of the channel. This arrangement serves to resist removal of the implant loop 16 from the channel 34, by providing a close fit with the loop.

This can be achieved by dimensioning the main part 78 of the channel 34 so that the width $W_1$ is slightly smaller than a cross-sectional width of the implant loop 16, at least in a relaxed (unloaded) state of the implant 12. In contrast, the width $W_2$ of the detent 44 is approximately the same as, and potentially slightly greater than, the cross-sectional width of the implant loop 16, at least in the relaxed state of the implant 12.

The implant loop 16 is therefore compressed slightly (in a direction transverse to its main axis) during entry into and transit along the main part 78 of the channel 34 from the open end 38 to the detent 44. The narrower width main part 78 of the channel 34 thus acts to resist transit of the implant loop 16 along the channel from the detent 44 to the open end 38. Entry of the loop leg 50 into the channel 34 may be facilitated by providing the open end 38 with an enlarged opening, for example by rounding edges 80 and 82 of the channel 34 adjacent the opening 38.

It will be understood that the first channel 32 is dimensioned in a similar way to the second channel 34 and so acts to on the implant 12 in a similar manner.

The fixation device 10 is approximately circular in plan view, taking the general form of a button. The channels 32 and 34 each extend inwardly from different points on the perimeter 40 of the fixation device, which in the circular button is its circumference.

The first portion 22 of the fixation device 10 is generally wedge or pie-shaped, comprising an outer surface 84 forming part of the perimeter 40 of the fixation device, and first and second inner surfaces 86 and 88 defining parts of the respective first and second channels 32 and 34. In the illustrated embodiment, the first and second inner surfaces 86 and 88 define side walls of the respective channels 32, 34. The outer surface 84 is arcuate and, in the case of the generally circular button shown in FIG. 1, is a radially outer surface having a substantially constant radius of curvature. The inner surfaces 86 and 88 are generally straight, extending inwardly along the respective channel axes 72 and 74.

The second portion 28 of the fixation device 10 is generally arcuate, forming a securing portion, which may take the form of a hook or hooking portion. The second, securing portion 28 receives the second end 46 of the implant loop 16, so that the implant 12 can be releasably coupled to the fixation device. This secures the second end 46 as described above, when the first and second legs 48 and 50 of the loop are located in the channels 32 and 34.

The second portion 28 comprises an outer surface 90 which forms part of the perimeter 40, and first and second inner surfaces 92 and 94 which define parts of the respective first and second channels 32 and 34. In the illustrated embodiment, the inner surfaces 92 and 94 define the side walls of the respective channels 32, 34. The outer surface 90 is arcuate, and in the case of the generally circular button shown in the drawings, is a radially outer surface of substantially constant radius of curvature.

The detents 42 and 44 defined by the closed ends of the channels 32 and 34 take the general form of an eye or eyelet which receive the legs 48 and 50 of the implant loop 16, the eyes indicated at 96 and 98 in FIG. 1, respectively. When the legs 48 and 50 of the implant loop 16 are positioned within the channels 32 and 34, and loading applied to draw the legs towards the closed ends 42 and 44 of the channels, the legs are drawn into the eyes 96 and 98 and so are laterally spaced from the axes 72 and 74 of the channels 32 and 34. This helps to maintain the legs 48 and 58 within the channels 32 and 34, positioned within the eyes 96 and 98. Centres or centroids (not shown) of the eyes 96 and 98 are typically spaced laterally from the channel axes 72 and 74.

The first and second surfaces 18 and 20 of the fixation device 10 are typically substantially planar, with the first portion 22, second portion 28 and bridge 30 all disposed in substantially the same plane. It will be understood however that one or more of the surfaces 18 and 20, but particularly the surface 20 (which faces away from the bone and which may form an upper or outer surface) may be curved, for example generally domed, in order to minimise a protrusion formed subcutaneously when the assembly 14 is implanted. Whilst the fixation device 10 is generally planar, peripheral edges forming the perimeter 40 may be rounded or chamfered as shown in FIG. 1. Similarly, surfaces forming the channels 32 and 34, eyelets 96 and 98, and openings to the apertures 24*a* to 24*d*, may also be rounded or chamfered.

In the illustrated embodiment, and as described above, the first portion 22 of the fixation device 10 comprises four apertures 24*a* to 24*d*. However, and as will now be described, the implant 12 may be coupled to the fixation device 10 using a minimum of two such apertures.

The implant 12 is of the general type disclosed in the applicant's earlier International patent application number PCT/GB2019/053385, filed on 29 Nov. 2019 and entitled "IMPLANT ASSEMBLY AND ASSOCIATED METHODS", the disclosure of which is incorporated herein.

The implant 12 is adjustable in length. In particular, the loop 16 that is formed when the implant 12 is coupled to the fixation device 10, has an adjustable length, even following implantation within the body. The ability to adjust the length of the loop 16 enables tension to be applied to the implant 12 to reduce the fixation device relative to the upper patella fragment 56, and to apply a compressive clamping force to the fragments 56 and 58, as discussed above.

The implant 12 is formed from a flexible elongate element which is coupled to the first portion 22 of the fixation device 10 in order to form the loop 16. The flexible elongate element is indicated by reference numeral 100 in the drawings, and is coupled to the first portion 22 of the fixation device 10 using the apertures 24*a* to 24*d*. Specifically, the flexible elongate element 100 passes from the second surface 20 side of the fixation device 10 through the aperture 24*a* and to the first surface 18 side of the device. The flexible element 100 then passes from the first surface 18 side through the aperture 24*b* back to the second surface 20 side, to form the loop 16. The second end 46 of the loop is thus formed by the portion which extends from the first surface 18 side of the fixation device 10.

Figure 8:
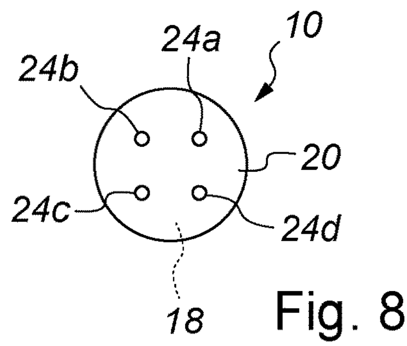
FIG. 8 is a plan view of the fixation device shown in FIG. 1, drawn in a simplified fashion with certain parts of the device not shown, for illustration purposes.
Figure 9:
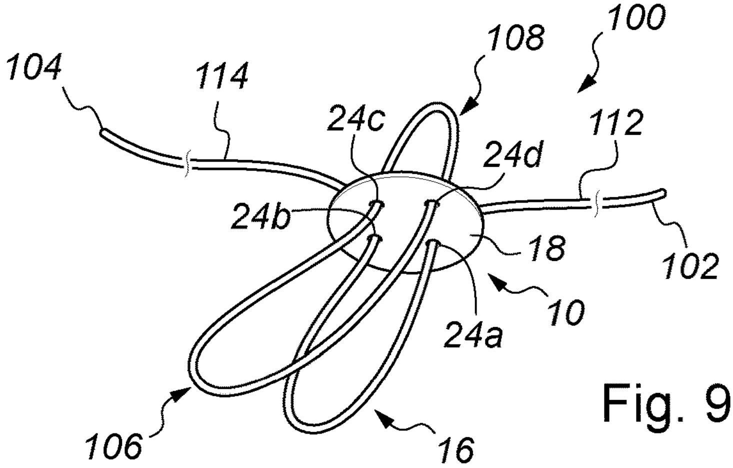
FIGS. 9 and 10 are perspective views of the implant assembly of FIG. 2, taken from below and from above respectively, with the fixation device shown in the simplified form corresponding to FIG. 8, and illustrating steps in a method of coupling the implant to the fixation device.
Figure 10:
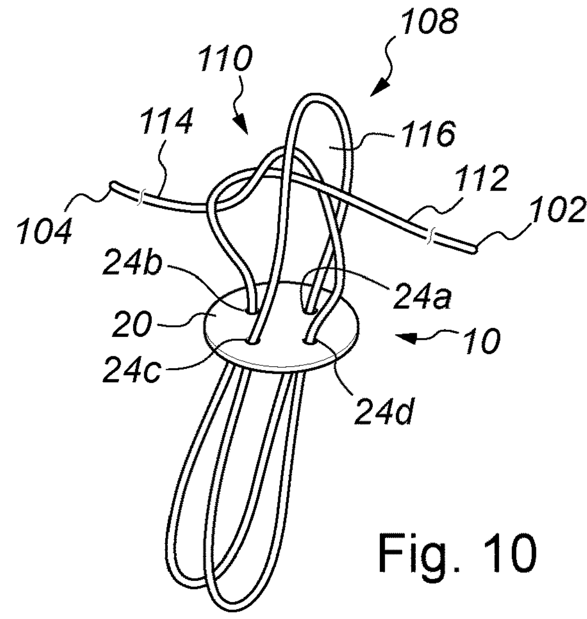

The specific method by which the implant 12 is secured to the fixation device will now be described in more detail, with reference to FIG. 8, which is a simplified view of the fixation device 10 showing just the apertures 24*a* to 24*d*, and with other features including the second portion 28, bridge 30 and channels 32 and 34 removed, for illustration purposes. FIGS. 9 and 10 are perspective views taken from below and from above, respectively, showing the implant assembly 14, and so the implant 12 coupled to the fixation device 10.

The flexible elongate element 100 has a first free end 102 and a second free end 104, and passes through the apertures 24*a* to 24*d* of the fixation device 10 so that two bone side loops 16 and 106 are formed. In the illustrated embodiment, the bone-side loop 16 forms a support loop and comprises the second end 46 which is secured by the fixation device 10. The second bone-side loop 106 is shortened so that it is reduced into contact with the bone surface 18 side of the fixation device 100, as will be described below.

The method of securing the implant 12 to the fixation device 10 involves taking the first free end 102 of the flexible element 100 and passing it down from the outer surface 20 side of the fixation device through the first aperture 24*a*. The free end 102 is then passed up from the bone facing surface 18 side through the aperture 24*b*. At this time, both of the free ends 102 and 104 reside on the second surface 20 side. The second free end 104 of the element 100 is then passed across the device 10 and down through the aperture 24*c* to the bone facing surface 18 side. The free end 104 is then passed up from the bone facing surface 18 side through the aperture 24*d*. This forms the bone-side loops 16 and 106, as well as a fixation loop 108.

A knot 110 can then be formed, using legs 112 and 114 of the flexible element 100 which comprise the free ends 102 and 104. An overhand knot is typically formed. The legs 112 and 114 are passed through an eye 116 of the fixation loop 108, so that the knot 110 that is formed is positioned between the second surface 20 of the fixation device and the fixation loop. Sufficient tension is applied to the legs 112 and 114 in order to draw the knot 110 towards the second surface 20 of the fixation device.

Tension is then applied to the first bone-side loop 16, to draw the second bone-side loop 106 into contact with the bone facing surface 18 of the fixation device 10, and to draw the fixation loop 108 down towards the second surface 20 of the fixation device. This clamps the knot 110 between the second surface 20 and the fixation loop 108, and fixes a length of the bone side support loop 16. The length of the loop 16 can however be adjusted easily either before or during a surgical implantation procedure, by loosening the second bone side loop 106 and the fixation loop 108, and either feeding material from the legs 112 and 114 to the bone side loop 16, or pulling on the legs 112 and 114 to remove material from the bone side loop.

Once the implant 12 has been positioned as shown in FIG. 6 and its loop end 46 secured to the fixation device 10, tension can be applied to the implant to clamp the patella fragments 56 and 58, as described above. This is achieved by pulling on the free ends 102 and 104 of the elongate element 100, which effectively shortens the loop 16. Excess material in the legs 112 and 114 can then be removed if desired, and the ends suitably sealed for example using a deformable (e.g. heat-sealable) polymeric material.

Whilst the illustrated embodiment comprises four apertures 24*a* to 24*d*, the implant 12 can be secured to the fixation device 10 using only two apertures. Using the apertures 24*a* and 24*b* as an example, the first free end 102 would be passed down through the aperture 24*a* from the second surface 20 side to the first surface 18 side, before being passed back up through the aperture 24*b*, thereby forming the first bone side loop 16. The second free end 104 would then be passed down through the aperture 24*b* to the first surface 18 side, before being passed back up to the second surface 20 side through the aperture 24*a*. This would form the second bone side loop 106 as well as the fixation loop 108. The free ends 102 and 104 would then both reside on the second surface 20 side and the knot could be formed in the eye 116 of the fixation loop 108 as described above.

It is also conceivable that the bone side loops 16 and 106 can be formed by passing the flexible elongate element 100 down through one aperture and then back up through the same aperture. For example, the first free end 102 may be passed from the second surface 20 side through the aperture 24*a* to the first surface 18 side, and then returned to the second surface side back through the same aperture 24*a*, to form the loop 16. The second free end 104 may be passed through the aperture 24*b* in a similar manner, to form the second loop 106.

The implant 12 is suitably of a metallic material, which may be a metal or a metal alloy such as steel (in particular stainless steel), or titanium and alloys thereof. The implant 12 is therefore of a material having a yield strength which is significantly greater than polymeric materials that have typically been employed to form prior implants. The implant 12 is suitably a multifilament structure comprising filaments of a metallic material and/or which has the indicated yield strength, and may be of a braided or woven structure. In a variation however, the implant 12 may be formed by twisting the filaments together.

The inventors have recognised that there are many scenarios in which relatively flexible implants can be made using an implant which is a multifilament structure comprising filaments of metallic material. Implant of this type would have relatively high yield strength in tension, when compared to prior flexible polymeric implants, whilst being more flexible under transverse loading than prior malleable metallic implants (which tend to maintain a deformed shape in the absence of a relatively significant applied deformation load). The implant of the present disclosure may have a relatively high strength under applied loading, whilst being relatively easy to manipulate in a surgical procedure to implant it in the body of a patient.

The fixation device 10, implant 12 and implant assembly 14 have been shown and described above in relation to the repair of a fractured bone in which the loop 16 of the implant 12 passes through a tunnel in the fractured bone. The implant assembly 14 may however be used in the repair of alternative bone fractures which do not involve the formation of a tunnel in the bone. This is illustrated in FIGS. 11 to 14, which will now be described.

FIG. 11 is a front view of a long bone in the body, such as the tibia 118, which has suffered an oblique fracture, as indicated by the line 120 in the drawing. The fracture line 120 extends transverse to a length of the tibia 118. Repair of the tibial fracture employing the implant assembly 14 involves a "cerclage" procedure, in which the implant 12 is passed around external surfaces of fragments 122 and 124 of the tibia 118, around an entire outer perimeter of the bone.

The tibial fragments 122 and 124 are correctly aligned and then secured using an appropriate clamping assembly (not shown), in a similar fashion to the patella 52 discussed above. The implant assembly 14 is then introduced so that the fixation device is proximate the first fragment 122 (or alternatively the second fragment 124), in the vicinity of the fracture 120. The loop 16 of the implant 12 is then directed around the outer perimeter of the tibia 118, so that it passes around portions of an outer surface 126 of the first fragment 122, and an outer surface 128 of the second fragment 124, as shown in FIG. 12. The loop 16 is then passed towards the fixation device 10, and is secured to the device by positioning the second end 46 of the loop in the first and second channels 32 and 34, passing over the bridge 30, as described in detail above. This is shown in FIG. 13. The loop 16 can then be shortened as described above to clamp the tibial fragments 122 and 124 together. Spare portions of the implant legs 112 and 114 can again be trimmed away and ends sealed, as described above.

The implant assembly 14 also has a use in the repair of dislocated joints, including the acromioclavicular joint (ACJ), and syndesmotic joints including the syndesmotic ankle joint between the tibia and fibula. In such scenarios, the implant 12 may be employed to reduce two bones in a joint which have become displaced from their proposer positions, for example due to torn or partially torn connecting tissue (i.e. a ligament or ligaments extending between the bones). Location and subsequent tensioning of the implant assembly 14 within the joint can enable the bones to be reduced to their proper positions.

For example, and in the case of a dislocation to an ACJ, the implant 12 may be located so that its loop 16 extends through a bone tunnel in a clavicle of the joint, with the fixation device 10 located on an upper (or superior) surface of the clavicle. The implant loop 16 can be passed around a coracoid process of the ACJ, before being directed back up the tunnel in the clavicle and secured to the fixation device 10 in the fashion described above. Tension can then be applied to reduce the clavicle to its proper position relative to the coracoid process.

A similar procedure can be carried out in other bone joint repairs, including syndesmotic joints.

In the patella repair method shown in FIGS. 4 to 7 and described above, the method may involve directing the end 46 of the implant loop 16 from the second end 66 of the tunnel 60 to a corresponding second end 67 of the other tunnel 62. The loop 16 is then passed up through the tunnel 62 and exits the tunnel through a first end 65. The loop 16 is then passed to the fixation device 10, and the loop end 46 secured to the second portion 28 of the fixation device. The implant 12 therefore passes from the first portion 20 of the fixation device 10 and through both of the tunnels 60 and 62 before returning to the fixation device, so that the implant loop 16 passes in a generally coronal plane, following a generally rectangular or square path (depending of course on the relative orientation of the tunnels and the shape of the patella 52). The fragments 56 and 58 may then be clamped together when tension is applied to the loop 16. A single implant assembly 14 may therefore be employed to effect the repair.

The implant 12 may comprise a plurality of yarns or strands, forming a braided or woven structure. Suitably, the implant 12 may comprise at least about 10 and up to about 20 yarns or strands, particularly between about 12 and about 20 strands. Each yarn or strand typically comprises a plurality of filaments, which may be monofilaments, the filaments being twisted together to form the yarn/strand. Suitably each yarn or strand comprises at least about 10 filaments, and up to about 20 filaments. An exemplary yarn/strand comprises 19 filaments. Each filament may have a thickness (which may be a diameter) of at least about 20 microns, and up to about 30 microns.

The braided structure may comprise a first set of fibres passing in a first direction around a circumference of the implant 12, and a second set of fibres passing in a second direction around the circumference of the implant. The first fibres may be disposed transverse to the second fibres, and transverse to a longitudinal axis of the implant. Braid angles may be defined between the fibres and the longitudinal axis. Reference is made to the discussion of a braided structure in PCT/GB2019/053385.

In the case of a woven implant structure, the structure will typically comprise a plurality of longitudinal yarns or strands (warps), and a plurality of transverse yarns or strands (wefts) arranged transverse, suitably perpendicular, to the longitudinal yarns. The longitudinal yarns extend along/parallel to a main length direction of the implant 12. The woven structure can be provided as a substantially flat tape. The woven structure can be substantially tubular. The tubular woven structure may comprise one or more side openings. The tubular woven structure may comprise ends which are of reduced width, which may facilitate entry of the ends into a tubular section of the woven structure. Reference is made to the applicant's prior International Patent Publication nos. WO-2009/109778A2, WO-2013/186525A1 and WO2017/013431A1.

There are substantial differences between the metallic multifilament implants and implant assemblies disclosed in this document and prior cables/ropes used for bone cerclage, which are used for the purpose of approximating bone fragments and maintaining them in their aligned position until healing has occurred. The prior ropes/cables are not sufficiently pliable, and suffer from numerous disadvantages as discussed above, including requiring the use of an array of cumbersome instruments for tensioning, crimping, and cutting the ropes to effect a repair.

In contrast, the implant (comprising a loop) described in this document can have one of two basic structures.

The first structure is a braid comprising yarns or strands as outlined above. The disclosed structure is sufficiently flexible to encircle a bone curvature under light tension. The loop is adjustable as described, and once secured in the fixation device, slackness in the loop can be taken up by manually applying tension on the two free ends of the elongate element used to form the loop, and which are coupled to the fixation device. This reduces the gap between the bone fragments, and maintains them in their aligned position until healing has taken place. Excess free ends of the implant forming the loop can be easily cut, e.g. with scissors.

The second structure is a woven structure comprising longitudinal yarns (warp ends) and weft using similar yarns or strands to those used in the braid. This second structure may be a flat tape, a tubular structure, with side openings and with ends reducing in width to allow the passage of the reduced ends within the tubular section.

The implant, fixation device and implant assembly disclosed in this document are illustrated during use in the repair of patellar fractures, or of an oblique bone fracture, as shown in FIGS. 5 to 7 and 11 to 14. There are, however, numerous other applications where the implant, fixation device and implant assembly could be readily used, optionally in conjunction with bone plates. Options including the repair of various fractures of the femur, and in stabilising the spine, e.g. by being secured to vertebral bodies of the spine.

Various modifications may be made to the foregoing, without departing from the spirit or scope of the present invention.

For example, the implant assembly may comprise two loops which have a support function. In the illustrated embodiments, this may be achieved by maintaining the two bone-side loops that are formed (16 and 106) to be substantially the same length, and providing each with a support function. In this situation, both loop ends would be secured to the fixation device, in the channels 32, 34 and over the bridge 30.

Reference is made primarily to the surgical procedures on the human body. It will be understood however that the fixation device, implant and implant assembly, and the techniques disclosed in this document, may have a use in the body of animals and so are not limited to the human body.

Reference is made to use of the implant assembly in repairing fractures of certain bones, and in the repair of dislocations of certain joints. It will be understood however that the fixation device, implant, implant assembly and techniques disclosed herein have a use in the repair of other bone fractures, and in the repair of other joint dislocations.

The first and second channels of the fixation may be curved, or at least partly curved. The first and second channels may define or describe an arc. The arcs may intersect at a location which is within the perimeter of the fixation device. The first and second channels may be disposed in a substantially U-shaped arrangement. The U-shaped arrangement may comprise a root, base or bottom. The root may be disposed between the closed ends of the channels, and may be defined by the bridge.

The apertures may be replaced with channels serving for receiving an assembled implant.

It will be understood that further, intermediate parts of the tunnel or tunnels may be provided in a further bone fragment or fragments, and which may align with the first and second tunnel portions. Where there is a further bone fragment or fragments, such may be clamped between the first and second fragments, and optionally (depending on the nature of the fracture) the loop may pass over part of a perimeter of the further fragment(s).

The first portion of the fixation device body may be disposed generally in a first plane, and the second portion may be disposed generally in a second plane which is different to the first plane. The second portion may extend out of a plane containing the first portion. The first and second planes may be disposed transverse to one another, optionally perpendicular.

In the illustrated embodiment this may be achieved, for example, by angling the bridge 30 of the fixation device 10 relative to the first portion 22, so that the second portion 28 stands up or out, away from a part of the upper surface 20 defined by the first portion. This may have the result that the part of the second loop end 46 coupled to the second portion 28 (around the bridge 30) may be spaced away from the surface of the bone, which may reduce frictional contact.

Whilst elongate metallic flexible implants have been primarily described, it should be appreciated that non-metallic flexible implants such as elongate polymeric flexible implants could be used to advantage with the fixation device.

Other embodiments of fixation device that may be used with an implant as generally or specifically described herein are shown in FIGS. 15 to 18. One or other of the embodiments described may be preferred dependent upon the particular use application.

In the embodiment shown in FIG. 15, the fixation device 210 comprises a generally circular device having a body 270 extending between a first surface 218 and a second surface 220. In this embodiment the device comprises a detent structure for coupling with the second end 46 of the loop the detent structure being in the form of an arcuate groove 236 for coupling with the second end of the loop, the arcuate groove preferably being at an outer perimeter of the device. The groove 236 is formed integrally with the fixation device and defines a perimeter about the apertures 224*a*, 224*b*, which extend through the body 270 of the device, the apertures being used to secure the other end of the loop implant in the same or similar manner to the first described embodiment. Again, in this embodiment, the apertures extend between the first and second surfaces 218, 220 and the detent structure (groove 236) is formed to extend between the first surface 218 and the second surface 220 of the fixation device 210. The body of the device is formed to have cut-away notches 225 within which lengths of the flexible elongate implant sit in order to avoid fouling with the patient, thereby enabling the fixation device to sit flush with the bone or tissue. The closed loop end 46 of the flexible implant nests within the groove 236, the implant extending from the fixing apertures 224*a*, 224*b* around the bone/tissue and releasably looping to nest within the groove 236.

With reference to FIG. 16, in this embodiment the apertures 324*a*, 324*b*, 324*c* serve to enable ends of the implant to be secured to the body 370 of the device. The implant loops about the bone/tissue and the closed loop end 46 of the flexible implant loops to releasably nest within the hook return portion 390 of a hook formation 391. Again, in this embodiment, the apertures 324*a*, 324*b*, 324*c* extend through the fixation device body 370 between the first and second surfaces 318, 320 and the detent structure (groove hook formation 391) is positioned spaced (by a distance D1) from the first and second surfaces in the axial direction of the apertures, and the hook formation 391 comprises a hook return portion 390 spaced laterally away from the apertures (Arrow A) in a direction transverse to the axial direction of the apertures.

In the embodiment of fixation device 410 disclosed in FIGS. 17 and 18, the device again employs a hook portion 491 to releasably secure the closed loop end 46 of the flexible implant. The apertures 424*a*, 424*b*, 424*c* and 424*d* serve to enable ends of the implant to be secured to the body 470 of the device. The stem 480 of the fixation device can be inserted into a bone tunnel up to the gap 481, such that surface 418 faces the bone and surface 420 faces away from the bone. The implant loops about the bone/tissue and the closed loop end 46 of the flexible implant loops to releasably nest within the hook return portion 490 of the hook formation 491, by passing through the gap 481. Again, in this embodiment, the apertures 424*a*, 424*b*, 424*c*, 424*d* extend through the fixation device body 470 between the first and second surfaces 418, 420 and the detent structure (groove return 490 of the groove hook formation 491) is positioned spaced (by a distance D2) from the first surface 418 in the axial direction of the apertures.

The invention claimed is:

1. An implant assembly for use in tissue repair, the implant assembly comprising:
- a fixation device having a body comprising:
  - a first surface adapted to face towards a bone;
  - a second surface adapted to face away from the bone; and
  - a plurality of apertures, each aperture extending through the fixation device body from the first surface to the second surface; and
- a flexible elongate implant coupled to the fixation device, the implant having a multifilament structure comprising filaments which are of a metallic or non-metallic material;
- in which the implant is coupled to the fixation device by passing through the apertures, and comprises a loop having a first end that is secured to the fixation device and a second end which can be releasably coupled to the fixation device following passage through or around a bone, for securing the implant assembly relative to the bone;
- in which the fixation device comprises a first portion comprising the plurality of apertures, the apertures cooperating to anchor the first end of the loop;
- in which the fixation device comprises a second portion coupled to the first portion via a bridge extending between the first and second portions;
- in which the fixation device comprises first and second channels located between the first and second portions, the channels each extending through the fixation device from the first surface to the second surface and having an open end disposed at a perimeter of the fixation device and a closed end disposed inwardly of the perimeter, the closed end defining a detent for the implant;
- in which the first and second channels are each elongate and substantially straight, having a longitudinal axis extending from the open end to the closed end, and in which the channels are arranged so that the axes are disposed transverse to one another; and
- in which the axes intersect at a location which is within the perimeter of the fixation device.

2. An implant assembly according to claim 1, wherein the detent couples with the second end of the loop.

3. An implant assembly according to claim 2, wherein the detent is formed integrally with the fixation device.

4. An implant assembly according to claim 2, wherein the detent is formed to extend between the first surface and the second surface of the device.

5. An implant assembly according to claim 2, wherein the detent comprises an arcuate structure for coupling with the second end of the loop.

6. An implant assembly as claimed in claim 1, in which the metallic material is selected from the group comprising a metal and a metal alloy.

7. An implant assembly as claimed in claim 1, in which the multifilament structure is a braided or woven structure.

8. An implant assembly as claimed in claim 1, in which the multifilament structure comprises a plurality of yarns, each yarn comprising a plurality of monofilaments.

9. An implant assembly as claimed in claim 8, in which the multifilament structure comprises from about 10 to about 20 yarns.

10. An implant assembly as claimed in claim 8, in which the yarns each comprise from about 10 to about 20 monofilaments, and in which the monofilaments each have a diameter between about 20 and about 30 microns.

11. An implant assembly as claimed in claim 1, in which each channel extends from the perimeter in a direction which is generally towards the other channel, the channels being disposed generally transverse to one another with the bridge located between their closed ends, the channels and the bridge cooperating to anchor the second end of the implant loop.

12. An implant assembly as claimed in claim 1, in which the first and second channels are disposed in a substantially V-shaped arrangement comprising a root disposed between the closed ends of the channels, the root being defined by the bridge.

13. An implant assembly as claimed in claim 1, in which the first portion is generally wedge-shaped, comprising an outer surface forming part of the perimeter of the fixation device, and first and second inner surfaces defining parts of the respective first and second channels.

14. An implant assembly as claimed in claim 13, in which the first and second inner surfaces define side walls of the respective channels.

15. An implant assembly as claimed in claim 1, in which the second portion is generally arcuate, and forms a hook portion which can receive the second end of the implant loop to anchor the second end.

16. An implant assembly as claimed in claim 1, in which the second portion comprises an outer surface forming part of the perimeter of the fixation device, and first and second inner surfaces defining parts of the respective first and second channels.

17. An implant assembly as claimed in claim 16, in which the first and second inner surfaces define side walls of the respective channels.

18. An implant assembly as claimed in claim 1, in which the detents take the form of an eyelet defined by the closed ends of the channels.

19. An implant assembly as claimed in claim 1, in which the first and second surfaces are substantially planar, and in which the first portion, second portion and the bridge are all disposed substantially in the same plane.

20. An implant assembly as claimed in claim 1, in which the first end of the implant loop is formed by a portion of the implant which extends from the second surface side of the fixation device, and the second end of the loop is formed by a portion of the loop which extends from the first surface side of the fixation device.

21. An implant assembly as claimed in claim 1, in which the implant comprises a flexible elongate element which is coupled to the fixation device to form the at least one loop, and in which the flexible elongate element passes from the second surface side of the fixation device and through one of the apertures to the first surface side, and from the first surface side through another one of the apertures back to the second surface side to form the at least one loop.

22. An implant assembly as claimed in claim 21, in which the flexible elongate element has a first free end and a second free end, and passes through apertures of the fixation device so that at least two bone-side loops are formed which each extend from at least one of the apertures at the first surface side of the fixation device.

23. An implant assembly as claimed in claim 22, in which at least one of the bone-side loops forms a support loop, and comprises the second loop end which is anchored by the fixation device.

24. An implant assembly as claimed in claim 21, in which at least one fixation loop is formed which extends from one of the apertures at the second surface of the fixation device to another one of the apertures at the second surface of the fixation device.

25. An implant assembly as claimed in claim 24, in which an adjustable knot arrangement is formed comprising an adjustable knot which is positionable on the second surface of the fixation device, a first leg extending from the knot to the first free end of the elongate element and a second leg extending from the knot to the second free end of the elongate element.

26. An implant assembly as claimed in claim 25, in which the flexible elongate element is securable to the fixation device by the fixation loop, the fixation loop passing over at least part of the adjustable knot arrangement to clamp the knot arrangement to the fixation device when the bone-side loop is tensioned relative to the fixation device.

27. An implant assembly as claimed in claim 1, in which the loop is adapted to be: located at least partly within a bone tunnel; located around an outer surface of a bone; or to pass around part of an outer surface of a bone.

28. An implant assembly as claimed in claim 1, in which the implant is adjustable in length.

29. An implant assembly as claimed in claim 28, in which the loop is adjustable in length.

30. An implant assembly for use in tissue repair, the implant assembly comprising:

a fixation device having a body comprising:
- a first surface adapted to face towards a bone;
- a second surface adapted to face away from the bone; and
- a plurality of apertures, each aperture extending through the fixation device body from the first surface to the second surface; and a flexible elongate implant coupled to the fixation device, the implant having a multifilament structure comprising filaments which are of a metallic or non-metallic material;

in which the implant is coupled to the fixation device by passing through the apertures, and comprises a loop having a first end that is secured to the fixation device and a second end which can be releasably coupled to the fixation device following passage through or around a bone, for securing the implant assembly relative to the bone;

in which the fixation device comprises a first portion comprising the plurality of apertures, the apertures cooperating to anchor the first end of the loop;

in which the fixation device comprises a second portion coupled to the first portion via a bridge extending between the first and second portions;

in which the fixation device comprises first and second channels located between the first and second portions, the channels each extending through the fixation device from the first surface to the second surface and having an open end disposed at a perimeter of the fixation device and a closed end disposed inwardly of the perimeter, the closed end defining a detent for the implant; and in which: the channels each comprise a main part having a width; and the detents of each channel have a width which is greater than the width of their main parts.

31. An implant assembly for use in tissue repair, the implant assembly comprising:

a fixation device having a body comprising:
- a first surface adapted to face towards a bone;
- a second surface adapted to face away from the bone; and
- a plurality of apertures, each aperture extending through the fixation device body from the first surface to the second surface; and a flexible elongate implant coupled to the fixation device, the implant having a multifilament structure comprising filaments which are of a metallic or non-metallic material;

in which the implant is coupled to the fixation device by passing through the apertures, and comprises a loop having a first end that is secured to the fixation device and a second end which can be releasably coupled to the fixation device following passage through or around a bone, for securing the implant assembly relative to the bone;

in which the fixation device comprises a first portion comprising the plurality of apertures, the apertures cooperating to anchor the first end of the loop;

in which the fixation device comprises a second portion coupled to the first portion via a bridge extending between the first and second portions;

in which the fixation device comprises first and second channels located between the first and second portions, the channels each extending through the fixation device from the first surface to the second surface and having an open end disposed at a perimeter of the fixation device and a closed end disposed inwardly of the perimeter, the closed end defining a detent for the implant; and in which the fixation device is generally circular in plan view, and the channels each extend inwardly from a point on the circumference of the fixation device.

* * * * *